(12) United States Patent
Deutschle et al.

(10) Patent No.: US 9,598,195 B2
(45) Date of Patent: Mar. 21, 2017

(54) PACKAGING STRUCTURE AND METHOD FOR STERILE PACKAGING CONTAINERS FOR SUBSTANCES FOR MEDICAL, PHARMACEUTICAL OR COSMETIC APPLICATIONS AND METHODS FOR FURTHER PROCESSING OF CONTAINERS USING THIS PACKAGING STRUCTURE

(71) Applicant: SCHOTT AG, Mainz (DE)

(72) Inventors: Gregor Fritz Deutschle, Wiesbaden (DE); Edgar Pawlowski, Stadecken-Elsheim (DE); Joern Wassenberg, Mainz (DE); Kai Wissner, Hirschberg (DE); Andreas Reisse, Regensburg (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 14/584,510

(22) Filed: Dec. 29, 2014

(65) Prior Publication Data
US 2015/0183541 A1 Jul. 2, 2015

(30) Foreign Application Priority Data
Dec. 27, 2013 (DE) .......................... 10 2013 114 896

(51) Int. Cl.
*B65D 81/24* (2006.01)
*B65B 55/18* (2006.01)
(Continued)

(52) U.S. Cl.
CPC .............. *B65B 55/18* (2013.01); *A61L 2/208* (2013.01); *A61L 2/26* (2013.01); *B65B 5/06* (2013.01);
(Continued)

(58) Field of Classification Search
CPC .... B65D 1/36; B65D 25/108; B65D 77/0426; B65D 75/527; A61J 1/16; A61L 2/208
See application file for complete search history.

(56) References Cited

U.S. PATENT DOCUMENTS 4,155,454 A 5/1979 Ryden
4,676,377 A * 6/1987 Rainin .................... B01L 3/021
206/468
(Continued)

FOREIGN PATENT DOCUMENTS

DE 102012103896 A1 11/2013
EP 1526088 A2 4/2005
(Continued)

*Primary Examiner* — Anthony Stashick
*Assistant Examiner* — James Way
(74) *Attorney, Agent, or Firm* — Ohlandt, Greeley, Ruggiero & Perle, LLP

(57) ABSTRACT

A method for sterile packaging of a plurality of containers is provided that includes: providing a carrier in which a plurality of receptacles are formed, the receptacles being formed by a closed bottom and a circumferential side wall, the upper ends of the receptacles, which are opposite to the respective bottom, are open and circumferential connecting webs are provided at the upper ends; placing the containers in the receptacles; providing a gas-impermeable protective foil; bonding the protective foil along the connecting webs with the upper surface of the carrier to package all the receptacles with the containers accommodated individually therein; and sterilizing the receptacles with the containers accommodated therein and/or the inner volumes of the containers by a gas flowing into the receptacles and/or into the inner volumes of the containers through at least one gas-permeable portion.

15 Claims, 13 Drawing Sheets

(51) Int. Cl.
*B65B 5/06* (2006.01)
*B65B 51/10* (2006.01)
*B65D 25/10* (2006.01)
*B65D 75/52* (2006.01)
*A61L 2/20* (2006.01)
*A61L 2/26* (2006.01)
*B65D 77/04* (2006.01)
*A61J 7/00* (2006.01)

(52) U.S. Cl.
CPC ............ *B65B 51/10* (2013.01); *B65D 25/108* (2013.01); *B65D 75/527* (2013.01); *B65D 77/0446* (2013.01); *B65D 81/245* (2013.01); *A61J 7/0069* (2013.01); *A61L 2202/182* (2013.01)

(56) References Cited

U.S. PATENT DOCUMENTS

| | | | | |
|---|---|---|---|---|
| 5,372,252 | A * | 12/1994 | Alexander | A61B 19/0288 206/210 |
| 6,050,400 | A * | 4/2000 | Taskis | B65D 81/266 206/204 |
| 6,098,802 | A * | 8/2000 | Asa | B01L 9/543 206/443 |
| 6,164,044 | A * | 12/2000 | Porfano | B65B 55/10 422/28 |
| 6,228,324 | B1 * | 5/2001 | Hasegawa | A61L 2/208 206/364 |
| 7,431,157 | B2 * | 10/2008 | Porret | A61L 2/08 206/363 |
| 7,910,067 | B2 * | 3/2011 | Knight | B01L 9/06 211/71.01 |
| D685,272 | S | 7/2013 | Stevens | |
| 2002/0104773 | A1 * | 8/2002 | Kalvelage | B65D 43/0212 206/538 |
| 2005/0226763 | A1 | 10/2005 | Raynal-Olive et al. | |
| 2007/0151882 | A1 * | 7/2007 | Cocheteux | A61M 5/008 206/366 |
| 2008/0251411 | A1 | 10/2008 | Walker et al. | |
| 2009/0220687 | A1 * | 9/2009 | Marks | B65B 61/025 427/207.1 |
| 2012/0118777 | A1 * | 5/2012 | Kakiuchi | A61M 5/002 206/366 |
| 2014/0027333 | A1 | 1/2014 | Pawlowski et al. | |
| 2015/0306259 | A1 * | 10/2015 | Deutschle | A61B 50/30 422/3 |

FOREIGN PATENT DOCUMENTS

| | | |
|---|---|---|
| EP | 2092927 B1 | 8/2009 |
| EP | 2659979 A2 | 11/2013 |
| WO | 01/34469 A2 | 5/2001 |
| WO | 03103728 A1 | 12/2003 |
| WO | 2007038488 A2 | 4/2007 |
| WO | 2008067576 A2 | 6/2008 |
| WO | 2009120393 A1 | 10/2009 |
| WO | 2011104385 A1 | 9/2011 |
| WO | 2013110107 A1 | 8/2013 |

* cited by examiner

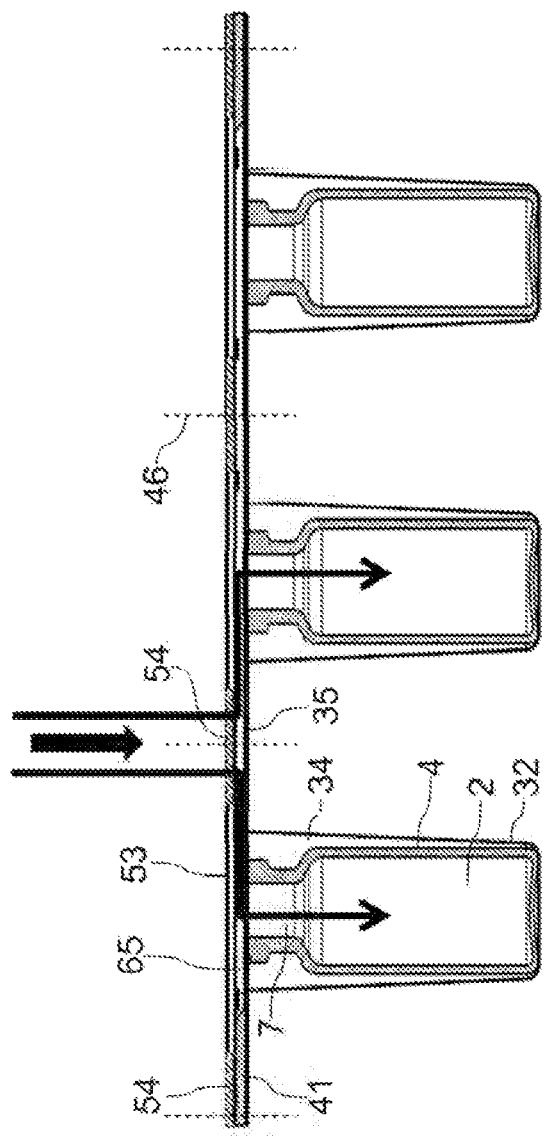

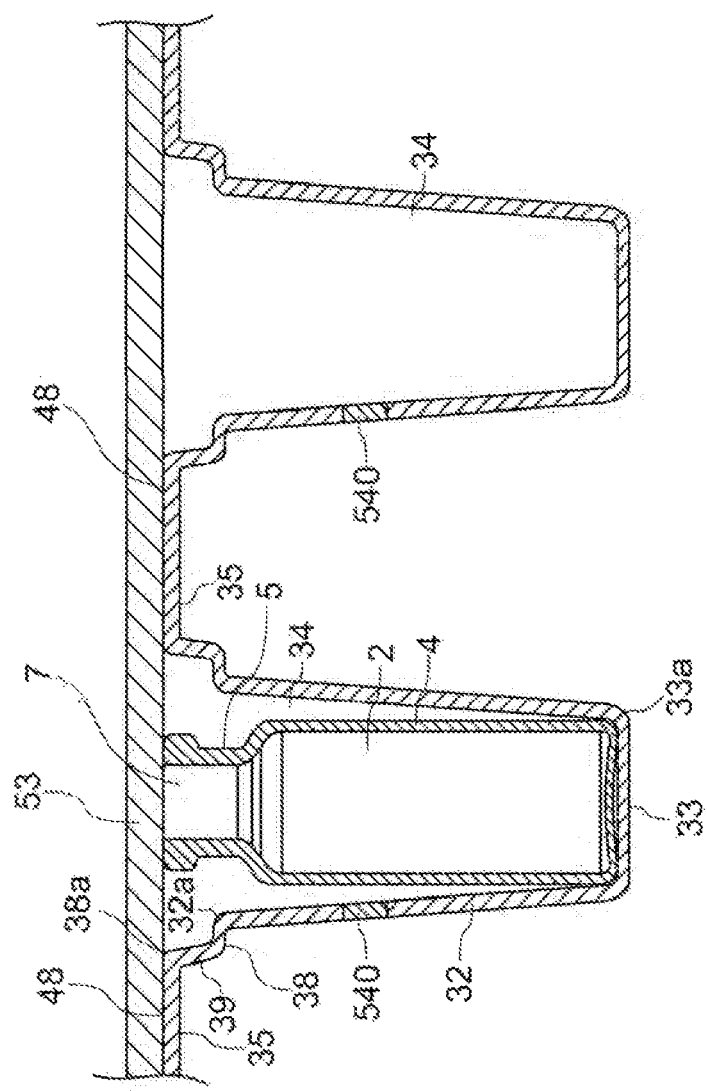

PACKAGING STRUCTURE AND METHOD FOR STERILE PACKAGING CONTAINERS FOR SUBSTANCES FOR MEDICAL, PHARMACEUTICAL OR COSMETIC APPLICATIONS AND METHODS FOR FURTHER PROCESSING OF CONTAINERS USING THIS PACKAGING STRUCTURE

CROSS REFERENCE TO RELATED APPLICATIONS

The present application claims the priority of German Patent Application 10 2013 114 896.4 "packaging structure and method for sterile packaging containers for substances for medical, pharmaceutical or cosmetic applications and methods for further processing of containers using this packaging structure", filed on Dec. 27, 2013, the entire content of which is hereby incorporated by way of reference.

FIELD OF THE INVENTION

The present invention relates generally to sterile packaging a plurality of containers for storing substances for medical, pharmaceutical or cosmetic applications, in particular of vials, ampoules or cartridges, and relates in particular to a packaging structure in which containers can be sterilized in a simple manner and the containers can be subsequently transported safely, sterile and without glass-to-glass contact.

BACKGROUND OF THE INVENTION

FIG. 14a of German patent application DE 10 2012 103 896 A1 of the applicant discloses a packaging structure for containers for medical, pharmaceutical or cosmetic applications, which are located in the receptacles of the packaging structure. The packaging structure is packaged sterile against the environment by applying protective foil that is selectively permeable to gas. A gas can flow in through the protective foil to sterilize the receptacles and/or inner volumes of the containers by fumigation. In order to remove individual containers, the protective foil must be broken. In this state, the containers are no longer kept sterile. If only a single container or a few containers are to be removed, the remaining container must be either disposed or sterilized and packaged again prior to their further processing to meet strict hygiene regulations.

US 200802511411 A1 discloses a blister packaging for inhalant drugs, wherein the drugs are inserted directly into concave cavities of a substrate which is sealed with a foil. The packaging of individual drug dosages can be broken individually or separated from the blister pack. With this blister pack it is, however, not possible to accommodate containers for medical, pharmaceutical or cosmetic applications in the concave cavities.

WO 2011104385 A1 discloses a display packaging of paperboard or cardboard comprising a display window for visual inspection of the stored drug. The drugs are in turn packaged in sterile packaging. Accommodating a plurality of drug dosages in the display packaging is not disclosed.

EP 2092927 B1 discloses a packaging unit comprising several blister packs that can be stored in an automated high-bay storage and output individually. However, accommodating containers for medical, pharmaceutical or cosmetic applications in blister packs is not possible.

WO 2013110107 A1 discloses a drug packaging for accommodating a plurality of blistered units having an antenna for automatically reading-out information concerning the units. A separation of the blistered units and sterilizing the inner volumes of the medication packaging are not disclosed.

With regard to the packaging and sterile transport of containers for medical, pharmaceutical or cosmetic applications, there exists the need for further improvement.

SUMMARY OF THE INVENTION

It is an object of the present invention to provide an enhanced packaging structure for sterile packaging a plurality of containers for medical, pharmaceutical or cosmetic applications, which can be produced in a simple and cost-effective manner and can be used more flexibly. According to further aspects of the present invention, there are to be provided a corresponding method for sterile packaging a plurality of containers, a method for the treatment or processing of containers using such a packaging structure as well as the use of a protective foil for such a packaging structure.

According to a first aspect of the present invention there is provided a method for sterile packaging of a plurality of containers fir medical, pharmaceutical or cosmetic applications, comprising the steps of: providing a carrier in which a plurality of receptacles are formed, wherein the receptacles are each formed by a closed bottom and a circumferential side wall, the upper ends of the receptacles, which are opposite to the respective bottom, are open and circumferential connecting webs are provided at the upper ends of the receptacles; placing the plurality of containers in the receptacles of the carrier; providing a gas-impermeable protective foil; connecting the protective foil along the connecting webs with the upper surface of the carrier to package all the receptacles with the containers accommodated individually therein; and sterilizing the receptacles with the containers accommodated therein and/or the inner volumes of the containers by a gas flowing into the receptacles of the carrier and/or into the inner volumes of the containers through at least one gas-permeable portion, wherein the at least one gas-permeable portion is formed as a portion of the gas-impermeable protective foil or of the packaging structure.

The containers can be transported in the packaging structure safely, sterile and without glass-to-glass contact to one another. Preferably weakening regions are embedded or formed in the packaging structure between the individual packaging subunits, e.g. by punching or laser machining of the material of the packaging structure. Thus, individual packaging subunits each having only one receptacle can be separated from the packaging structure in a simple manner, wherein the containers are still accommodated in the receptacles of the packaging subunits sterile and sealed against the environment. In contrast to the prior art a packaging structure, which has been opened, must therefore not be fully processed or used anymore. The receptacles can be arranged with high packing density in an array on the carrier.

According to a preferred embodiment the receptacles are sterilized by a gas flowing through at least one gas-permeable portion formed in the protective foil or connected with the protective foil in a suitable manner. According to a further embodiment, the selectively gas-permeable portions may also be formed directly in the side walls or bottoms of the receptacles of the packaging structure.

According to a further aspect of the present invention a correspondingly designed packaging structure is provided as set out below.

According to a further aspect of the present invention a method for sterile packaging of a plurality of containers for medical, pharmaceutical or cosmetic applications is provided, comprising the steps of: providing a carrier as set forth above; placing the plurality of containers in the receptacles of the carrier; providing a gas-impermeable protective foil, which may comprise at least one gas-permeable portion for sterile packaging the receptacles; connecting or bonding the protective foil along the connecting webs with the upper surface of the carrier for sterile packaging all the receptacles with the containers accommodated individually therein and forming a packaging structure as described above.

According to a further preferred embodiment the receptacles may be sterilized subsequently by a gas flowing in through at least one gas-permeable portion, as described above.

According to a further embodiment, the packaging structure is preferably formed of a material which is resistant to hydrogen peroxide ($H_2O_2$) vapor (VHP). Special chemical-resistant plastics, such as polyamide (PA), polyethylene (PE), polycarbonate (PC), polypropylene (PP), PSU and PVC are suitable. Also a metal foil or aluminum foil is suitable. Particularly suitable is an aluminum-polypropylene composite material provided as a foil or sheet. Hydrogen peroxide (VHP), which has a sterilizing effect, can be produced in an advantageously simple and cost-effective manner by active evaporation of an aqueous hydrogen peroxide solution and may thus be used to sterilize the inner volume of the packaging structure and/or the inner volumes of the containers accommodated therein. In order to achieve a high biological decontamination rate of microorganisms, a defined high hydrogen peroxide concentration of 30% to 35% is required.

According to a further aspect of the present invention a method for treatment or processing of containers for medical, pharmaceutical or cosmetic applications using a packaging structure as described above is provided, comprising the steps of: providing the packaging structure having a plurality of receptacles, in each of which a container is accommodated and sterile packaged; removing or opening the protective foil of at least one receptacle of the packaging structure; treatment or processing of the respective container of the at least one receptacle; and applying the protective foil, which has been removed or opened previously, or another protective foil for sealing the at least one receptacle, preferably for sterile sealing the at least one receptacle.

A further aspect of the present invention relates to the use of a protective foil comprising at least one gas-impermeable portion and at least one gas-permeable portion as described above, for producing such a packaging structure.

OVERVIEW ON DRAWINGS

The invention will now be described in an exemplary manner and with reference to the accompanying drawings, from which further features, advantages and problems to be solved will become apparent. In the drawings:

FIG. 3b shows a schematic sectional view flow paths, along which a gas flows when sterilizing the packaging structure according to the FIG. 3a by fumigation;

FIG. 4c shows a packaging structure according to a further embodiment of the present invention in a schematic sectional view;

In the drawings, identical reference numerals designate identical or substantially equivalent elements or groups of elements.

DETAILED DESCRIPTION OF PREFERRED EMBODIMENTS

Figure 1:
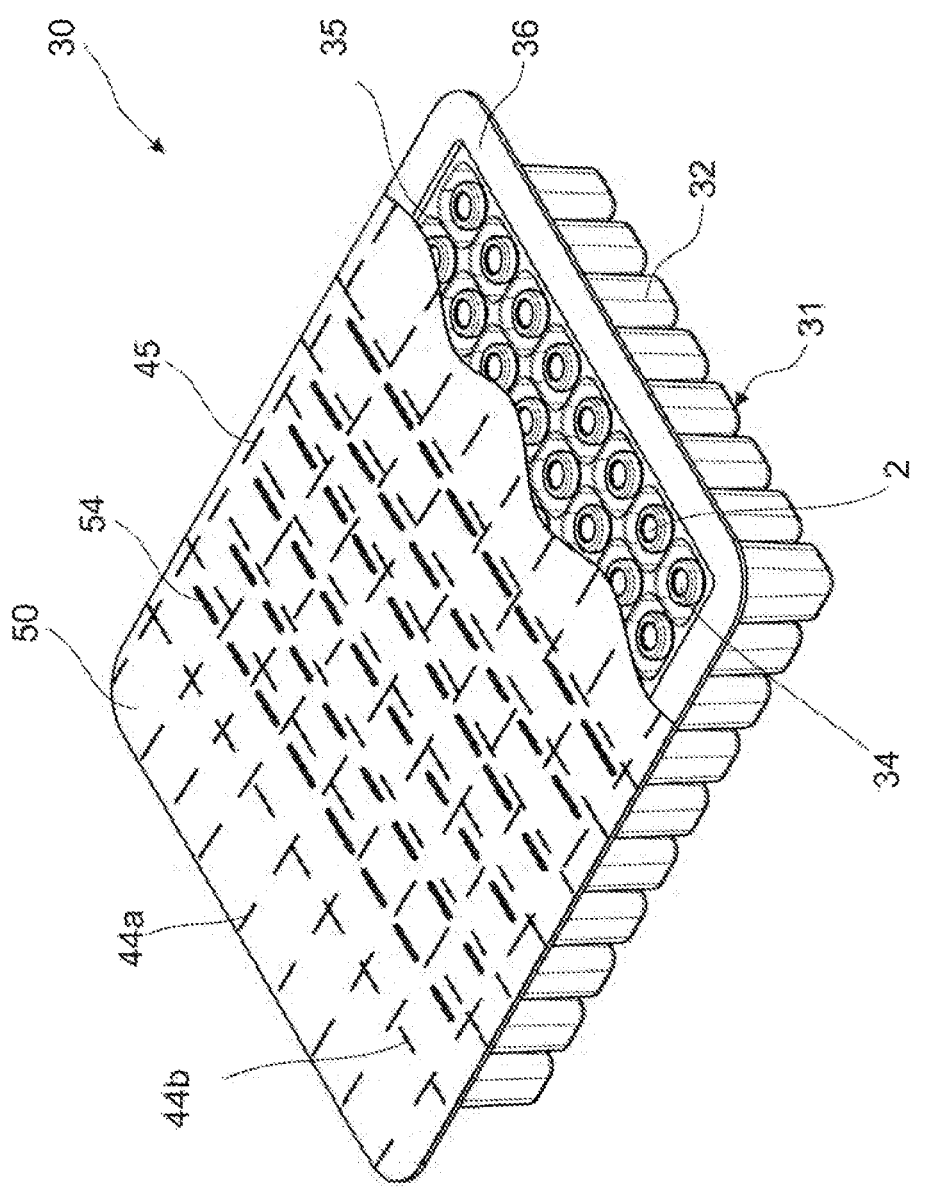
FIG. 1 shows a packaging structure according to a first embodiment of the present invention.

FIG. 1 shows a packaging structure according to a first embodiment of the present invention in perspective top view. The packaging structure 30 is formed by a carrier 31 and a protective foil 50, which is applied to the upper surface of the carrier 31, in particular adhesively bonded, sealed, heat-bonded or heat-sealed, or which is melted on it by heat, in particular by means of laser radiation or rf-radiation. The carrier 31 is preferably formed of a plastic, in particular by means of an injection molding process. This plastic can be flexible or rigid. The carrier 31 can also be formed from composite materials, for example from a cellulose-containing material in which a plastic tube is incorporated, which forms the inner walls of the receptacles.

In the substrate 31 a plurality of receptacles 34 are formed, each of which is formed overall like a tube and has a closed bottom 33 and an open upper end at the upper surface of the carrier 31. More specifically the receptacles are each formed by the closed bottom 33 and a circumferential side wall 32. At the upper ends of the receptacles 34 circumferential connecting webs 35 are provided, which together form the upper surface of the substrate 31 and which serve for connecting adjacent receptacles 34 with each other. The connecting webs 35 are preferably formed to be flat and have a material thickness, which defines a suitable mechanical stability or also flexibility of the connecting webs 35. The connecting webs 35 define an array of receptacles 34. These may be arranged in particular in a regular array of rows and columns of receptacles in particular.

The protective foil 50 has gas-impermeable portions 53 (see FIG. 3a), which are each formed above the receptacles 34 and extend over the entire associated receptacle 34 as well as over the associated circumferential connecting web 35 so that respective sterile packaged packaging subunits each having one receptacle 34 can be formed by connection of the protective foil 50 with the connecting webs 35, wherein the packaging subunits can be separated individually in each of which a single container 2 is accommodated and sterile packaged against the environment. For this purpose, weakening regions 44a, 44b may extend along the connecting webs 35 along which the connecting webs 35 can be separated mechanically, in particular broken off. Such weakening regions 44a. 44b may be formed along the connecting webs 35, for example as continuous, linear recesses or as a series of point-like recesses, for example by mechanical carving, embossing or laser treatment of the material of the connecting webs 35. However, such weakening regions are not absolutely necessary, since the packing subunits can be separated in other ways during further processing of the packaging structure, for example by mechanical severing or laser cutting.

In each of the receptacles 34 a single container 2 is arranged. The protective foil 50 is connected with the upper surface of the carrier 31 along the connecting webs 35 and the edge of the carrier 31 in such a manner that the containers 2 are sterile packaged in the receptacles 34 formed by the packaging subunits after connecting the protective foil 50 with the carrier 31 and that the packaging subunits can be severed from the carrier 31 in such a manner that each container 2 is still sterile packaged against the environment in the severed packaging subunits. For this purpose a sufficient width of the connecting regions must be ensured. It must be ensured that the severing process for severing or separating the packaging subunits takes place precisely along the connecting regions, in particular in the middle or substantially along the connecting regions. After separating the packaging subunits, the width of the connecting region of a respective receptacle must be sufficient to ensure a sterile packaging of the container accommodated in the receptacle.

If the packaging subunits are to be broken off mechanically, in particular manually, for this purpose the formation of the aforementioned weakening regions precisely along the connecting webs 35 is of advantage. Preferably, the weakening regions extend exactly in the middle along the connecting webs 35, so that a sufficient sterile packaging of the receptacles can be ensured even after separating the packaging subunits by specifying the widths of the connecting webs 35 and the overlap of the respective connecting regions with the connecting webs 35, as described below in more detail with reference to FIG. 4a.

Figure 3A:
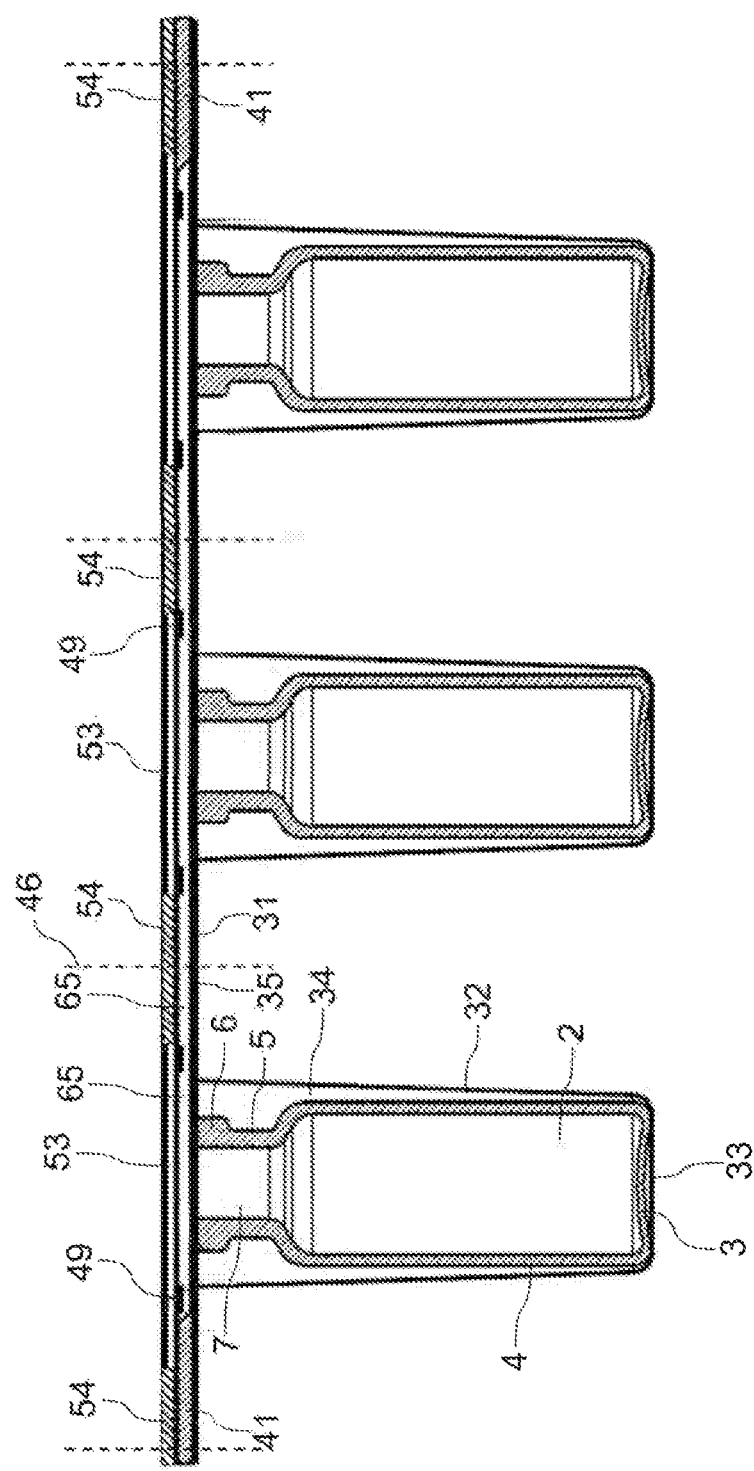
FIG. 3a shows a packaging structure according to a further embodiment of the present invention in a schematic sectional view.

An example of such containers embodied as vials is shown schematically in a sectional view according to FIG. 3a. The vials have a cylindrical basic shape, having a cylindrical side wall 4 with~within tolerances~constant inner and outer diameters, which project vertically from a flat vial bottom 3, which merges in a constricted neck portion 5 of a relatively short axial length near the upper open end of the vial and then merges in a widened upper rim 6, which has a larger outer diameter than the associated neck portion 5 and is configured for connection to a closure member. Such vials are radially symmetric and are made of a transparent or colored glass or of a suitable plastic material by blow molding or plastic injection molding techniques, and can be in general internally coated so that the material of the vial emits minimal impurities to the agent to be received.

Other examples of medication containers in the sense of the present application are ampoules, cartridges and syringes or injection containers.

In the sense of the present invention, such containers are used for storage of substances or agents for medical, pharmaceutical or cosmetic applications, which are to be stored in one or several components in solid or liquid form in the container. Especially in the case of glass containers storage periods can amount many years, notably depending on the hydrolytic resistance of the glass type used. While, in the following, cylindrical containers are disclosed, it should be noted that the containers, in the sense of the present invention, may also have a different profile, for example a square profile, rectangular profile or polygonal profile.

As can be seen in FIG. 3a, the side walls 32 of the receptacles may converge conically or otherwise toward the bottom end and may have an inner diameter at the bottom end, which virtually corresponds to the outer diameter of the containers 2 to be accommodated, so that the container 2 can slide easily into the receptacles 34 and are arranged automatically centered on the bottom 33. As shown in FIG. 4b, a step 38 may also be formed at the upper end of the receptacles 34, at which the receptacle is expanded and limited by a circumferential upper side wall 39 having a larger diameter. In this manner, the containers can be gripped more easily at their upper ends for removal.

As shown in FIG. 1, the protective foil 50 comprises a plurality of strip-shaped gas-permeable portions 54, which are each associated with a receptacle 34 of the carrier 31. In the illustrated array or matrix arrangement of the receptacles 34 shown in FIG. 1, the gas-permeable portions 54 are arranged extending in parallel with the transverse sides 34 of the carrier 31, wherein the gas-permeable portions 54 do not extend over the entire length of the transverse side of the carrier 31. According to a first embodiment, the gas-permeable portions 54 are formed of a selectively gas-permeable plastic foil, in particular of a meshwork of synthetic fibers, for example polypropylene-fibers (PP), or of a Tyvek® protective foil. According to an alternative embodiment, the selectively gas-permeable portions 54 are formed as lattice-like structures having openings, for example as a grid, which are formed of plastic webs, which intersect each other with a predetermined grid pitch. After sterilization of the receptacles and/or of the containers such grid-like structures are then closed by means of a gas-impermeable portion, e.g. by bonding a gas-impermeable foil onto the respective portions with the grid-like structures. The gas-impermeable portions of the protective foil 50 associated with the receptacles 34 are formed, for example, of a plastic foil or metal foil or a composite of these materials. The gas-permeable portions 54 and the gas-impermeable portions may also be formed as an integral composite material.

Figure 2:
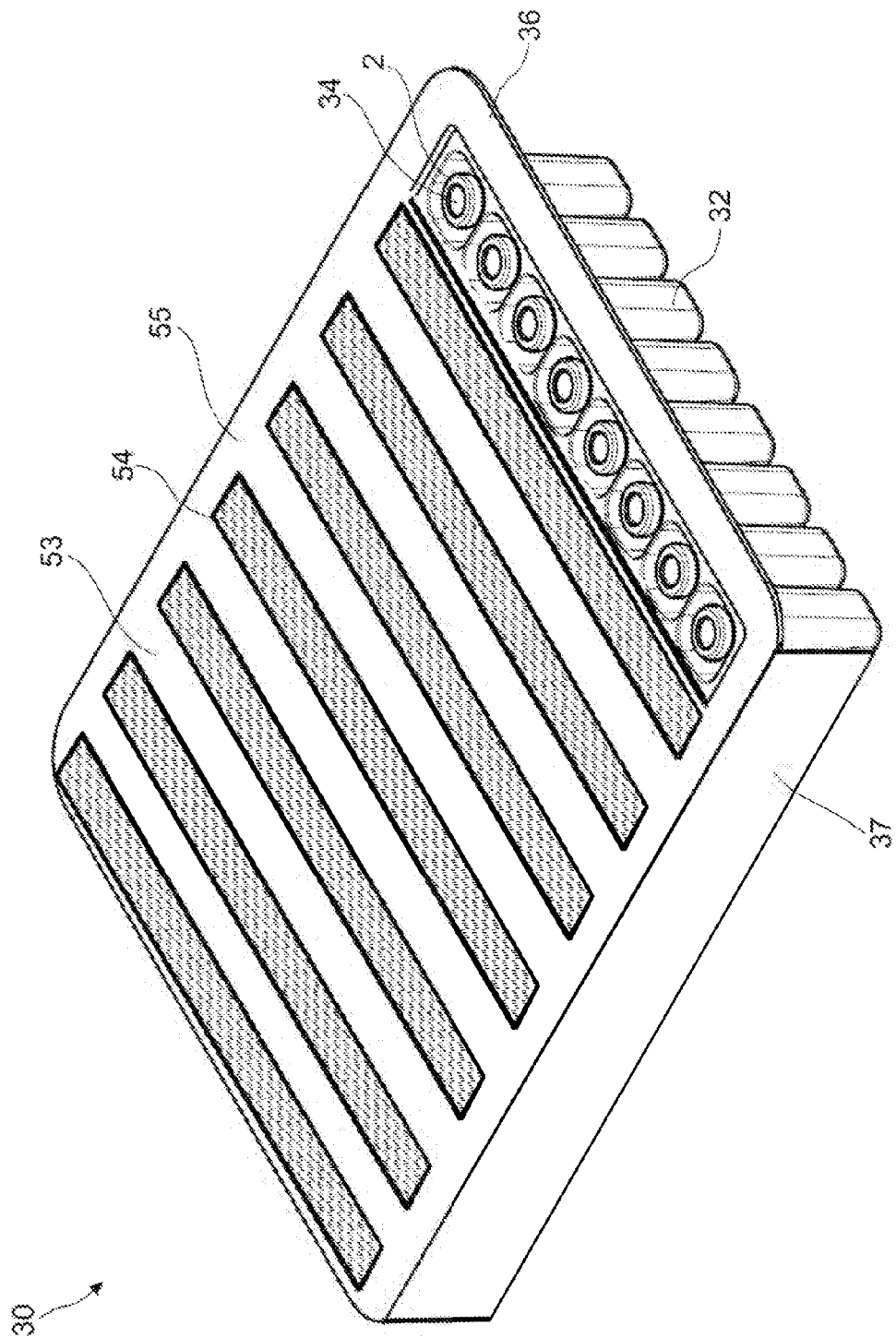
FIG. 2 shows a packaging structure according to a further embodiment of the present invention.

FIG. 2 shows a further embodiment of a packaging structure 30, in which the gas-permeable portions 54 are formed as strips extending along the entire transverse side of the carrier 31 and in parallel with and spaced to the columns of receptacles 34 of the carrier 31. Respective connecting webs 35 are formed between the strips of gas permeable portions 54 and the receptacles, which form the upper surface of the carrier 31, which are formed circumferential and which surround the receptacles 34. The gas-impermeable portions 53 completely cover the receptacles 34 and also form the edges of the protective foil 50. In contrast to FIG. 1, in the embodiment of FIG. 2 additional covers 37 are provided extending along the longitudinal sides (optionally also along the transverse sides) of the carrier 31, which serve for an additional mechanical protection of the carrier 31.

Figure 4A:
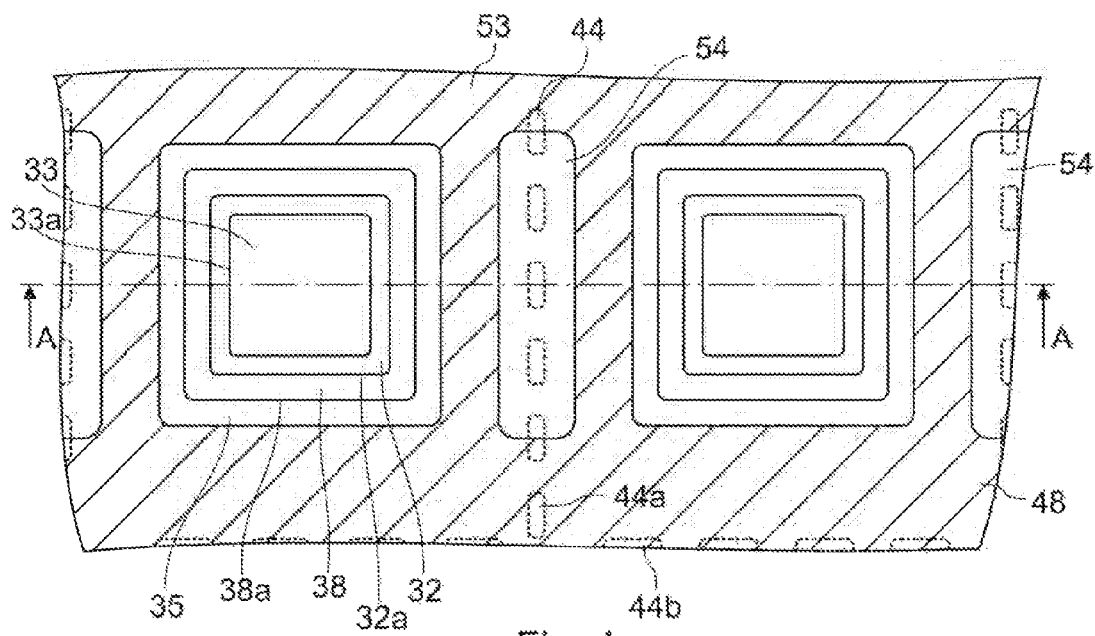
FIGS. 4a-4b show a packaging structure according to a further embodiment of the present invention.
Figure 4B:
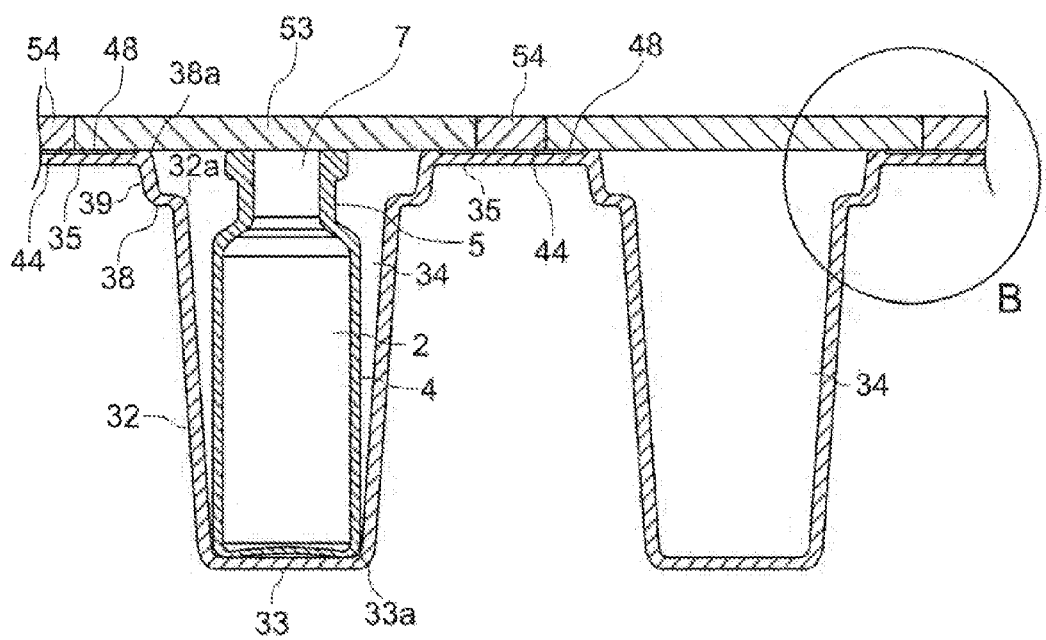

FIG. 4a is an enlarged plan view of two receptacles 34. In particular the contour 33a of the bottom 33, the contour 32a of the cylindrical side wall 32 of the receptacles 34 and the contour 38a of the step 38 are shown. According to FIG. 4a each receptacle 34 is surrounded by a circumferential connecting web 35, which are used to connect the receptacles 34 with each other. The receptacles may be surrounded by a region, where the protective foil 50 is not connected to the connecting webs 35. In the other regions 48 of the connecting webs 35, however, the protective foil 50 is fully connected with the connecting webs 35. The connection is chosen such that each of the receptacles 34 of the carrier 31 are respectively sealed gas-tight and sterile against the gas-permeable portions 54 and the edge of the carrier. This may include for example the following connecting techniques: heat-bonding or heat-sealing by means of an adhesive between the protective foil 50 and the connecting webs; partially fusing together the protective foil 50 with the connecting webs 35 or with an adhesive or connecting material applied thereto, for example by applying heat and fusing of plastic materials. The connecting regions 48 surround the receptacles 34 completely. The width of the connecting portions 48 is chosen to be sufficient so that the receptacles 34 are still sealed reliably and gas-tight and sterile against the environment, even after separation of the individual packaging subunits with the individual receptacles 34.

In the example of FIG. 4a, the separation of individual package subunits, each having one receptacle 34, by mechanical breaking along the horizontal weakening lines 44a and vertical weakening lines 44b is performed, for example, by forming recesses by mechanical embossing or laser machining along the connecting webs 35. The horizontal weakening lines 44a and the vertical weakening lines 44b are formed according to the matrix array of receptacles 34 and preferably extend exactly along the center line of the respective connecting webs 35. The sectional view of FIG. 4b shows weakening regions 44 in the form of concave recesses, which are formed in the lower surfaces of the connecting webs 35.

In the example of FIG. 4a the selectively gas-permeable strip 54 is formed exactly symmetrical with regard to the horizontal weakening line and communicates with the left and right receptacle 34. When severing the packaging subunits, these gas-permeable portions 54 are also severed, for which purpose similar weakening regions (not shown) may be formed in the gas-permeable portions 54.

Figure 7:
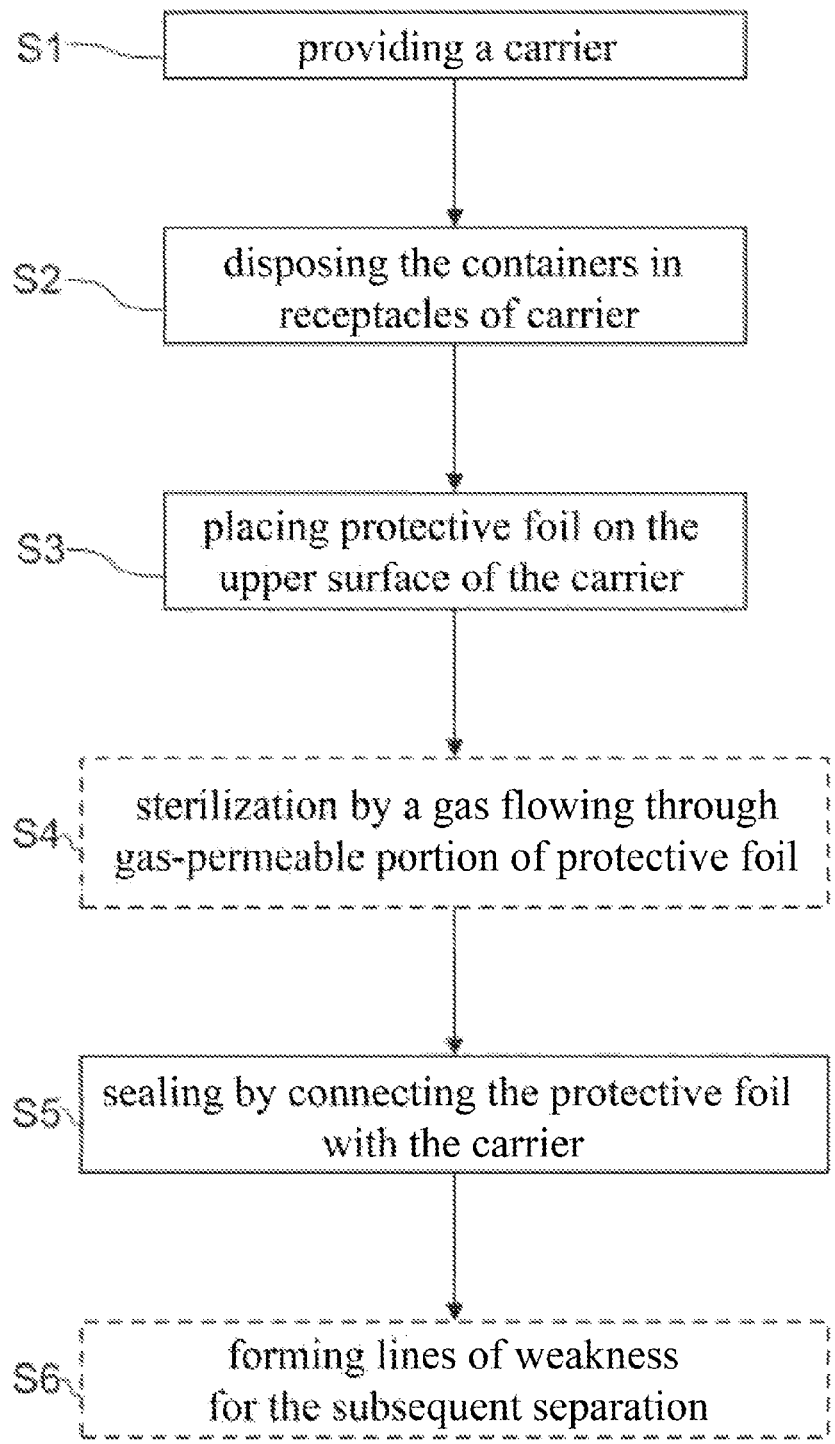
FIG. 7 shows a schematic flow diagram of a method for sterile packaging a plurality of containers according to the present invention.

Referring to the flowchart of FIG. 7 and the sectional views of FIGS. 3a and 3b, a method according to the present invention for sterile packaging a plurality of containers will be described in the following.

First, in the step S1, a carrier 31 is provided as described above with reference to FIG. 1. In the receptacles 34 of the carrier 31, the containers 2 are accommodated. The containers may already be filled and sealed.

Then, a protective foil 50 comprising a plurality of gas-impermeable portions 53 is provided for sterile packaging the receptacles in step S3. The protective foil 50 is arranged in such a manner with respect to the carrier 31, that the gas-impermeable portions 53 are arranged exactly above the receptacles, so as to cover them completely. Subsequently, in step S5, the protective foil 50 is connected with the upper surface of the carrier 31 along the connecting webs 35 to sterile package each of the receptacles 34 individually with the containers 2 accommodated therein and to form a packaging structure 30 as shown in FIG. 1 or 2. In the state shown in FIGS. 1 and 2, the containers can be transported sterile packaged and mechanically protected against the environment.

In a preferred embodiment of the method according to the present invention containers 2, which are still open and not filled, shall be sterile packaged and transported by means of the packaging structure 30. For this purpose, the receptacles 34 of the carrier 31 can be sterilized in step S4 by a gas flowing in after inserting the containers in step S2 and arranging the protective foil 50 on the upper surface of the substrate 31 in step S3, as described below.

Figure 6A:
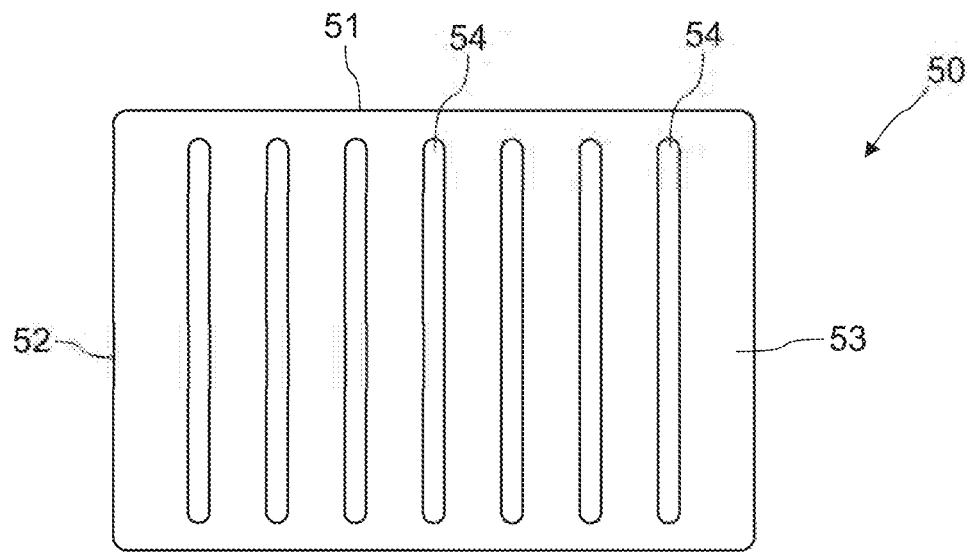
FIGS. 6a-6b show a protective foil according to further embodiments of the present invention in a plan view.
Figure 6B:
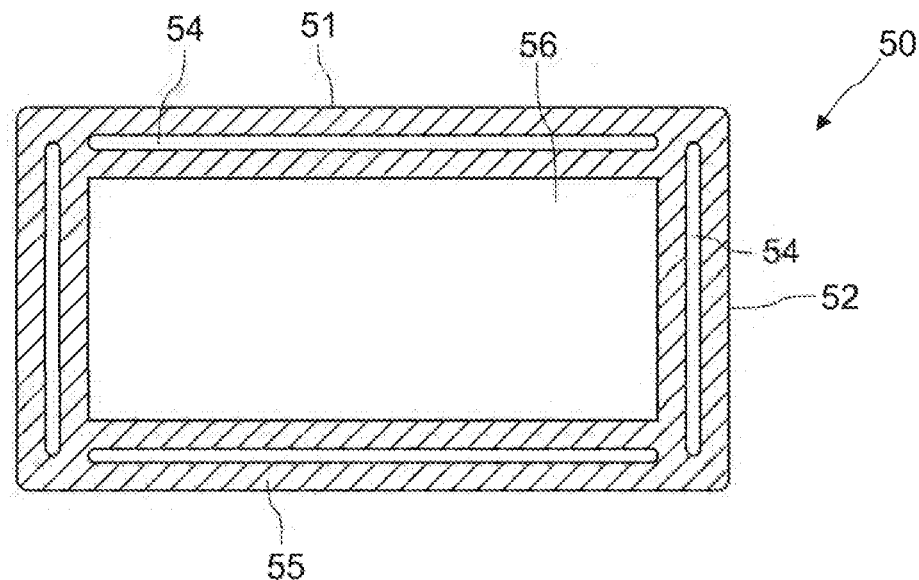

For fumigating the interior of the receptacles 34 a gas flows through the gas-permeable portions 54 of the protective foil 50. As shown in FIG. 3a, the receptacles 34 of the carrier 31 communicate with the respectively associated gas-permeable portion 54 via flow channels 65, which extend between the upper surface of the carrier 31 and the lower surface of the protective foil 50. For this purpose, distance or spacer members 41 are disposed on the upper surface of the carrier 31, which cause that a gap remains when placing the protective foil 50 onto the upper surface of the carrier 31 in step S3. Already in this state a circumferential connecting region may be formed along the longitudinal sides and transverse sides of the carrier 31, where the protective foil 50 is connected to the edges of the substrate 31, for example by heat-bonding, heat-sealing or thermal fusing of the materials of the protection foil 50 and the carrier 31. In this state, a circumferential frame is formed by the connecting region, which is shown for example in FIG. 6b and extends circumferentially along the longitudinal sides 51 and lateral sides 52 of the protective foil 50. This frame encircles the gas-permeable portions 54 completely, so that the gas, which flows through these portions 54 into the above-mentioned gap between the protective foil 50 and the upper surface of the carrier 31, cannot escape to the outside but must flow through the flow channels 65 into all associated receptacles 34 of the carrier 31 to sterilize the interior of the receptacles 34 and/or of the containers 2.

For sterilization, for example, ethylene oxide (ETO) at low temperatures (30° C.-60° C.) or hydrogen peroxide ($H_2O_2$) vapor (VHP) may be used. The latter acts sterilizing and may be generated through active evaporating an aqueous hydrogen peroxide solution. In order to achieve a high biological decontamination rate of microorganisms, preferably a defined high concentration of 30% to 35% hydrogen peroxide is used.

The arrows in FIG. 3b illustrate the flow pattern of the inflowing gas.

As will be readily apparent for the skilled person, the aforementioned flow channels may also be formed as suitably designed grooves or recess in the upper surface of the substrate 31 and/or the lower surface of the protective foil 50.

After sterilization of the receptacles 34 in step S4, the connecting of the protective foil 50 and upper surface of the substrate 31 is performed in the manner described above along the connecting webs 35 to sterile package each of the receptacles and seal them gas-tight against the respectively associated gas-permeable portion.

Subsequently, in step S6 weakening regions may be formed along the connecting webs 35 as described above by way of example with reference to FIG. 1.

Referring to FIGS. 5a to 5f in the following further details in forming a packaging structure according to further embodiments of the present invention will be described. In each case the area B is shown in a greatly enlarged partial sectional view.

Figure 5A:
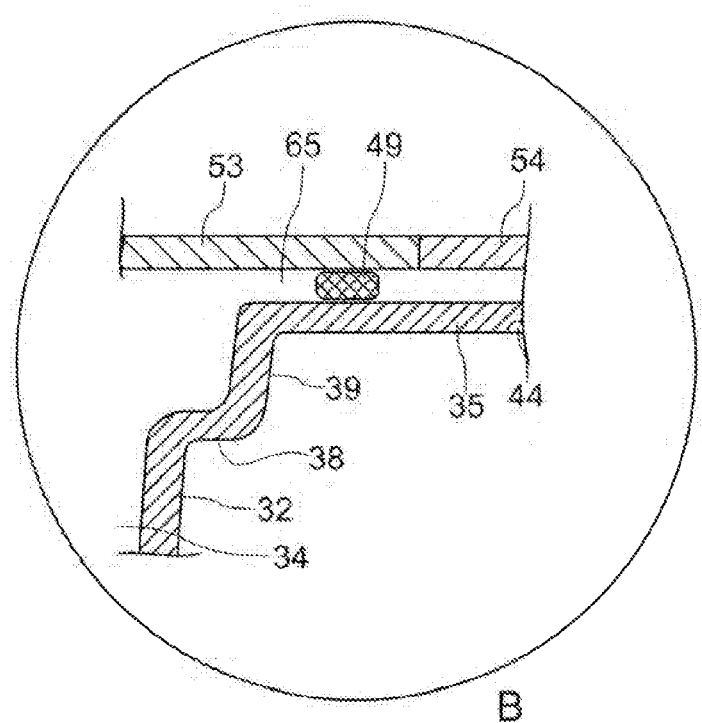
FIGS. 5a-5f show further details of a packaging structure according to further embodiments of the present invention in schematic partial sectional views.

According to FIG. 5a the adhesive strip 49 is interrupted in the region of the flow channel 65, which connects the receptacle 34 with the associated gas-permeable portion 54, allowing gas to flow freely through this region into the receptacle 34. The adhesive strip 49 may also be formed along the connecting webs by application of individual adhesive points at regular intervals. For bonding or connecting care must be taken to ensure that by a sufficient size of the adhesive drops and sufficient pressure and/or heat a circumferential connecting region 48 is formed, which is sufficiently wide and thick (see FIG. 4a) and seals the respective receptacle 34 completely against the associated gas-permeable portion 54 and the environment. As can be seen in FIG. 5a, the adhesive strip 49 also serves as a spacer member to define the height of the flow channel 65 suitably. In principle, it is also possible to omit all of the lateral spacer members 41 that are shown in FIGS. 3a and 3b.

According to FIG. 5a the gas-permeable portion 54 is located outside the contour of the adhesive strip 49, whereas the gas-impermeable portion 53 extends beyond the contour of the adhesive strip 49. After connecting the protective foil 50 and the carrier 31, the receptacle 34 is thus surrounded completely by the connecting region. According to FIG. 5a the weakening region embodied as a concave recess 44 is formed centrally beneath the gas-permeable portion 54 in the lower surface of the connecting web 35.

Figure 5B:
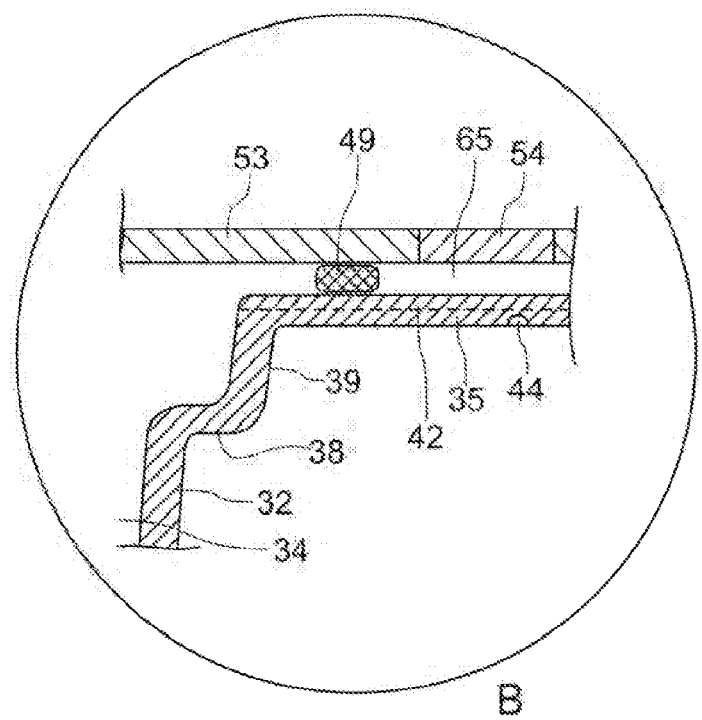

Deviating from FIG. 5a, in the embodiment of FIG. 5b an elongated recess or groove 42 is formed in the upper surface of the connecting web 35, which further connects the gas-permeable portion 54 with the interior of the associated receptacle 34 and through which the gas can also flow for the sterilization, whereby a sufficient flow cross-section of the flow channel 65 can be ensured even with a relatively thin adhesive strip 49. Of course, such a recess or groove may also be formed additionally or as an alternative in the lower surface of the protective foil 50. The recess or groove 42 is closed when connecting the protective foil 50 with the carrier 31, for example by an adhesive, which flows into the recess or groove 42.

Figure 5C:
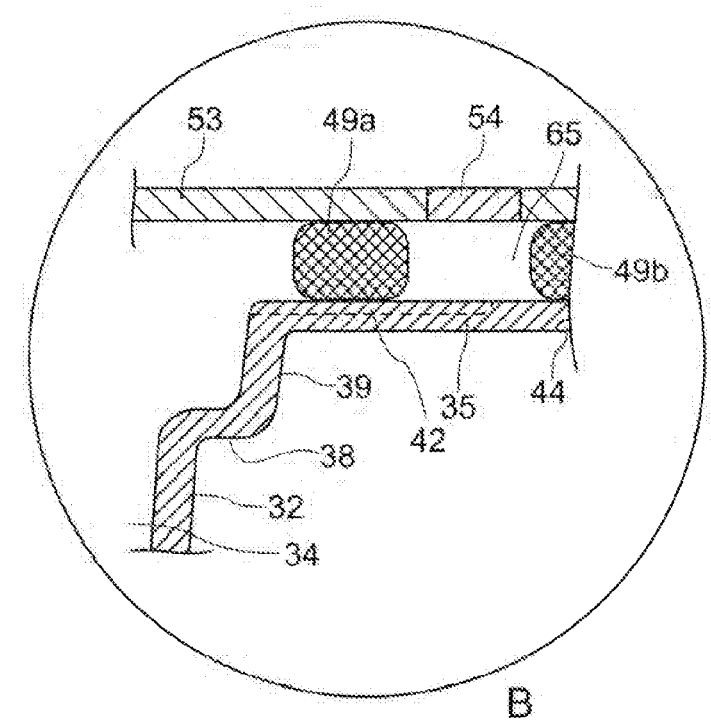

In contrast to the above embodiments, according to FIG. 5c an adhesive strip 49a, 49b is formed at both sides of the gas-permeable portion 54, so that the gas-permeable portion 54 can be sealed on both sides gas-tight and sterile against the receptacles at both sides of the gas-permeable portion 54. Again, a recess or groove 42 may be additionally provided, as described above.

Figure 5D:
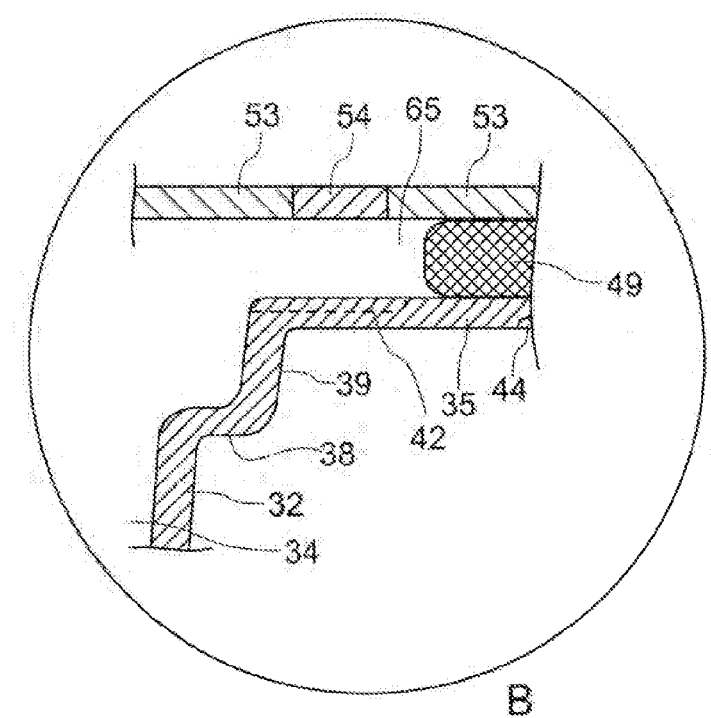

In contrast to the above embodiments, according to FIG. 5d the gas-permeable portion 54 is disposed within the circumferential adhesive strip 49 so that a relatively large flow cross-section can be provided for the flow channel 65. For connecting the protective foil 50 with the carrier 31 an adequate size of the adhesive strip 49 and/or a sufficient pressure and/or heat must be ensured so that the adhesive strip flows up to the edge of the upper side wall 39 of the receptacle to seal the receptacle completely gas-tight and sterile against the gas-permeable portion 54.

Figure 5E:
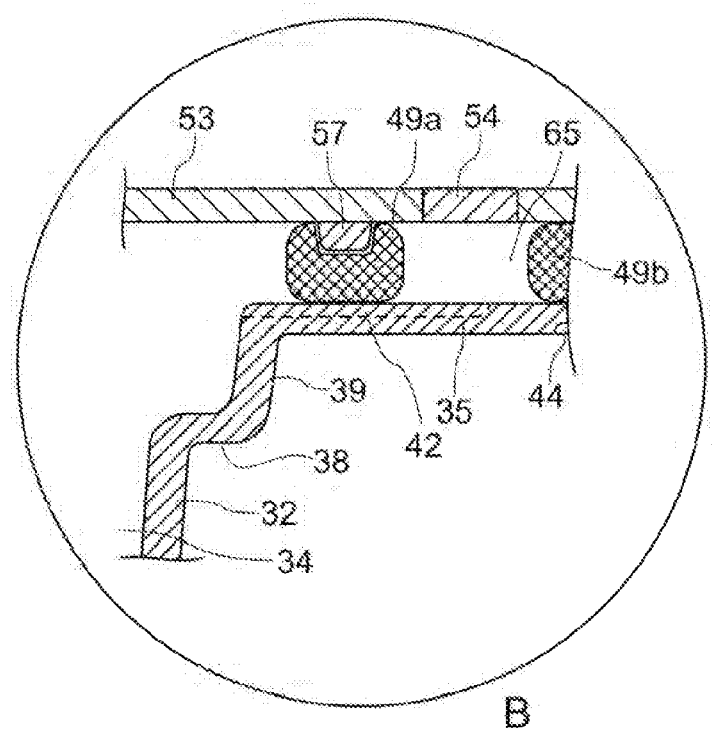

In contrast to the above embodiments, according to FIG. 5e a sealing plug 49a is provided on the lower surface of the gas-permeable portion 53, which is formed corresponding to the cross-section of the recess or groove 42. By applying pressure from above during joining of the protective foil 50 and the carrier 31 this sealing plug 49a is pushed into the associated recess or groove 42 to seal them jointly by the adhesive of the adhesive strip 49a flowing-in. The sealing plug 49a may be molded or attached to the lower surface of the gas-impermeable portion 53 as a plastic plug, or may be formed integrally with the gas-impermeable portion 53. If the recess or groove 42 is not formed in the connecting web 35 but in the lower surface of the protective foil 50, the sealing plug 49a is formed correspondingly on the upper surface of the connecting web 35.

Figure 5F:
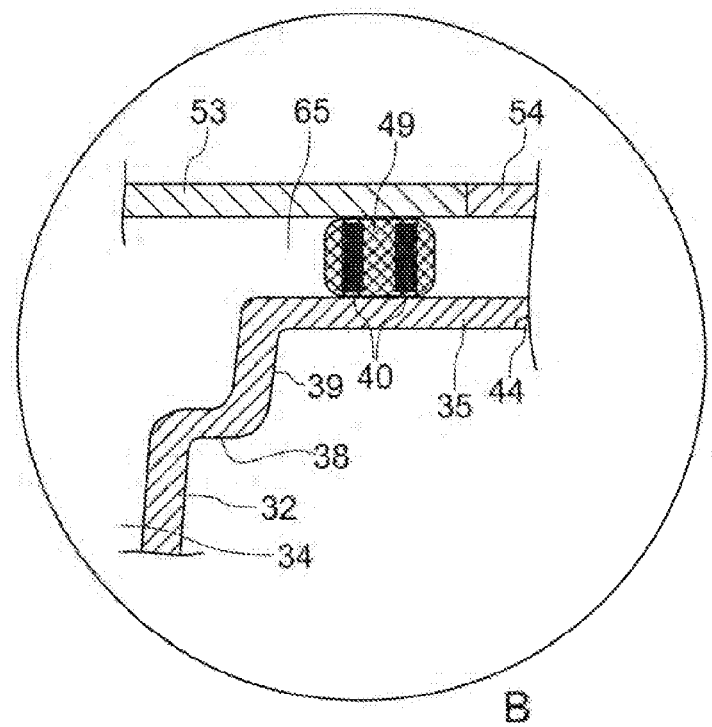

In contrast to the above embodiments, according to FIG. 5f additional spacer members 40 are provided in the area of the flow channel 65, to ensure an adequate flow cross-section. The spacer members 40 may be molded onto the lower surface of the protective foil 50 or onto the upper surface of the connecting webs 35, for example, as a plastic, or may be attached to them or may be formed integrally with these. The spacer elements 40 can be configured in such a manner that they can be broken-off or released, so that these are broken-off or released when a pressure is applied during the joining of the protective foil 50 and the carrier 31 so as to be embedded in the adhesive edge, which is formed circumferentially around the respective receptacles 34.

While it has been described above that the selectively gas-permeable portion is disposed in the protective foil, according to further embodiments the selectively gas-permeable portion may also be formed directly in the packaging structure. This is exemplified in FIG. 4c, which shows a packaging structure according to a further embodiment of the present invention in a schematic partial sectional view. In contrast to the embodiment of FIG. 4b, according to FIG. 4c the selectively gas-permeable portion 540 is formed directly in the cylindrical side wall 32 of a respective receptacle 34. In general, this can be accomplished by forming a recess in the cylindrical side wall 32 and closing the recess by connecting a selectively gas-permeable foil 540 with the cylindrical side wall 32. In embodiments in which the carrier of the packaging structure is formed of a composite material, this can also be implemented by embedding the selectively gas-permeable foil 540 in a plastic insert/tray or forming it, which is part of the composite material. Alternatively, the selectively gas-permeable portion 540 may be provided in the bottom 33 of the respective receptacle 34. Alternatively, the selectively gas-permeable portion 540 may be formed also annular so that it extends around the entire circumference of the respective receptacle 34. In such a case, the selectively gas-permeable portion 540 may also be arranged as a separate annular member between the protective foil 50 and the packaging structure. In the embodiments in accordance with this paragraph, thus the protective foil does not need to be provided with a gas-permeable portion. If necessary, the selective gas-permeable portions may be sealed after sterilization of the receptacles and/or containers by means of sterile gas-impermeable portions, for example by bonding gas-impermeable strips onto the respective gas-permeable portions 540.

Figure 6C:
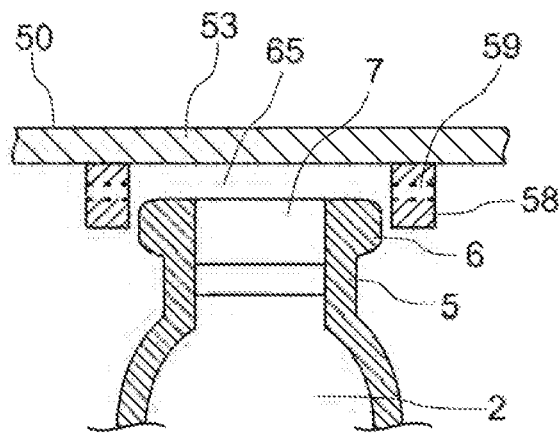
FIGS. 6c-6d show further details of a protective foil according to further embodiments of the present invention.
Figure 6D:
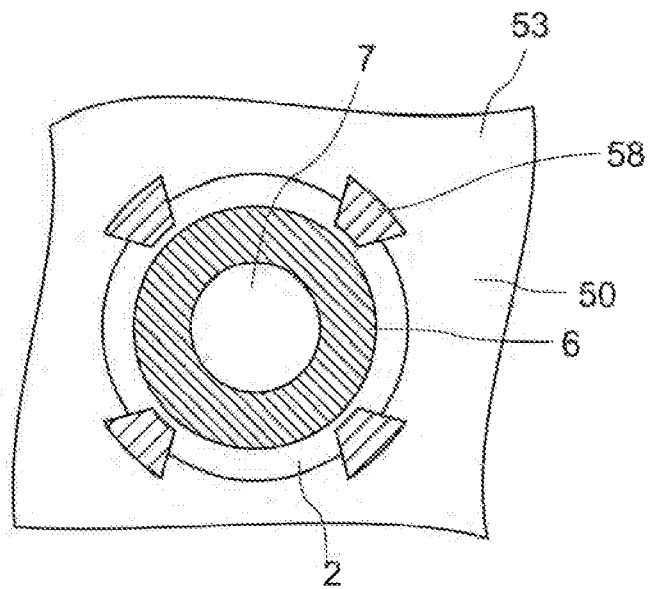

Referring to FIGS. 6c and 6d in the following further embodiments of the protective foil will be described. According to FIG. 6c centering and positioning means 58 are provided on the lower surface of the gas-impermeable portion 53 of the protective foil, which cooperate with the upper rim of the containers 2 accommodated in the receptacles of the carrier in such a manner that these are centered and suitably positioned in the receptacles. In order to enable the gas to flow into the inner volume of a container, flow channels 59 may be formed in these centering and positioning means 58. Such centering and positioning means 58 may be used in particular also as spacer members to ensure an adequate distance between the upper rim of the containers 2 to be accommodated and the lower surface of the gas-impermeable portion 53. For this purpose, the centering and positioning means 58 may in particular also be formed with a step (not shown) which extends in radial direction and inward beyond the upper rim 6 of the container 2.

FIG. 6d shows a further embodiment of such centering and positioning means 58, which are formed here as segments of a circle and which are preferably distributed at regular angular intervals from each other around the upper rim 6 of the container 2. Here, the gas flowing into the receptacles may flow into the inner volume of the container 2 through the gaps of adjacent centering and positioning means 58. Also here, the centering and positioning means 58 may have a stepped design, with a step (not shown) that extends in radial direction and inward beyond the upper rim 6 of the container 2.

In the state of FIG. 1 or 2, the containers accommodated in the receptacles of the packaging structure 30 can be transported packaged sterile and mechanically protected. The containers may be, for example, filled and/or empty vials, syringes and dual-chamber syringes or cartridges and dual-chamber cartridges or vartridges. These can be transported in the packaging structure even with different sizes (length and diameter) safely and without glass-to-glass contact. The side walls of the receptacles may be transparent, so that the containers accommodated in the receptacles are visible from the outside and may be assessed, inspected or tested visually or opto-electronically, for example by means of a laser beam or LED-beam or an optoelectronic detection device. In this manner, in particular also a visual package (blister) for concurrently accommodating a plurality of containers in receptacles of packaging subunits may be provided which can be separated individually as blister pack and sterile sealed, as described above. The containers may be stored upright, horizontal or upside down. The containers stored sterile in the packaging structure 30 may, of course, be further processed or treated after opening or removing the protective foil of at least one receptacle of the packaging structure 30. This further processing or treatment of the containers can be performed while they are still accommodated in the receptacles. Alternatively, this further processing or treatment of the containers may also be performed outside of the receptacles, for example in processing stations at which the containers are each taken out of the receptacles, processed further or treated and are finally inserted again back into the receptacles. By applying the protective foil previously removed or opened protective foil or another (a new) protective foil, the packaging structure can be closed again, preferably sterile sealed, as described above. To this end, the connection of protective foil and the carrier can be implemented using the same adhesive or sealant, which was used to form the packaging structure. Or a new adhesive or sealant is applied suitably for connecting the protective foil with the carrier. For forming again the packaging structure, the receptacles of the carrier can be sterilized again in the manner described above by a gas flowing through the gas-permeable portions of the protection foil or of the packaging structure.

The processing steps for the treatment or processing of the containers may be in particular any of the following steps: cleaning the containers, heat treatment of the containers, disinfection of the containers, filling the containers with a substance for medical, pharmaceutical or cosmetic applications, lyophilization of the substance, applying a closure cap onto a closure of the container, in particular a metal foil by beading or crimping, or applying a plastic cap and sealing the container, shaking or vibrating the container and/or weighing of the container between the individual process steps.

Figure 8:
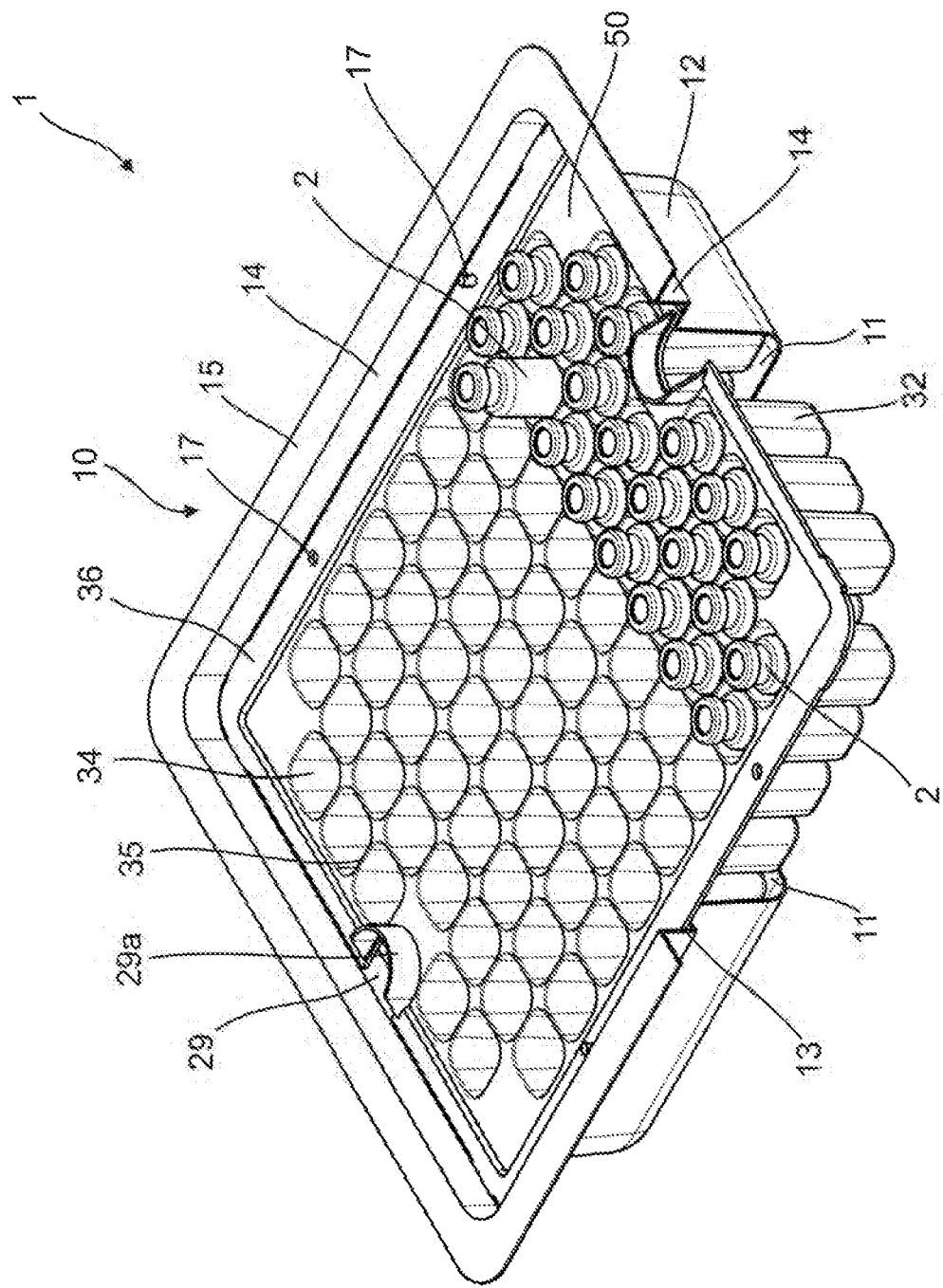
FIG. 8 shows a transport and packaging container in a perspective partial sectional view and in a plan view, in which a packaging structure according to a further embodiment of the present invention is accommodated.

A packaging structure 30 as described above can be transported in an additional transport and packaging container 10, as exemplified in FIG. 8. However, such a transport and packaging container is not mandatory for a sterile transport of the containers.

According to FIG. 8 the transport and packaging container 10 is substantially box-shaped or trough-shaped and comprises a bottom 11, a circumferential side wall 12 extending perpendicularly, a step 13 projecting substantially perpendicularly, a circumferential upper side wall 14 and an upper edge 15 on which a flange is formed. The upper side wall 14 may be formed inclined at a slight angle of inclination relative to a line perpendicular to the bottom 11 in order to facilitate the insertion of the packaging structure 30. Such a transport and packaging container 10 is preferably formed of a plastic material, in particular using plastic injection molding technology, and is preferably formed of a clear transparent plastic material to enable an optical inspection of the packaging structure 30 accommodated in the transport and packaging container 10 and of the containers 2 supported by it.

For accommodating the packaging structure 30 in the transport and packaging containers 10, this may be surrounded by a circumferential peripheral web. Such a peripheral web may also be formed in sections continuously along the peripheral edge. For a reliable positioning of the packaging structure 30 in the transport and packaging container 10, the packaging structure 30 and the transport and packaging container 10 comprise positioning structures that are cooperating with each other, in particular in a form-fitting manner. Thus, positioning structures in the form of protrusions or recesses (or cavities) may be formed at an appropriate location, particularly on the step 13 or on supporting surfaces 18 of the transport and packaging container 10, which cooperate in a form-fitting manner with correspondingly configured recesses (or cavities) or protrusions of the packaging structure for precisely positioning the packaging structure 30 in the transport and packaging container 10. For this purpose a plurality of pin-like protrusions may be formed particularly on the step 13 of the transport and packaging container 10, which cooperate with corresponding centering openings formed in a supporting frame of the packaging structure 30. According to FIG. 8, the step 13 of the transport and packaging container 10 is formed as a circumferential, planar supporting surface on which the packaging structure 30 is directly supported. According to further embodiments, also supporting surfaces 18 or supporting members may be formed on the side walls 12 of the transport and packaging container 10, in particular in the form of protrusions. In this way, the packaging structure 30 can be precisely positioned in the transport and packaging container 10 and in this way the plurality of vials 2 can be disposed and supported in a regular array and at precisely defined positions in a transport and packaging container 10 with standardized dimensions.

Although, in FIG. 8, the bottom 11 of the transport and packaging container 10 is shown to be closed and formed integral with the side wall 12, the lower end of the transport and packaging container 10 may also be open in the manner of the upper end, in particular provided with a flange-like lower edge in the manner of the upper edge 15.

As shown in FIG. 8, in the regular arrangement according to FIG. 8 the plurality of vials 2 is arranged in a matrix distributed along two mutually orthogonal directions at predetermined constant intervals with each other. In principle, also other regular arrangements are conceivable, for example adjacent rows or columns of receptacles may be mutually offset to each other by a predetermined lengths to each other, namely in a periodic arrangement having a predetermined periodicity. Thus, automated manufacturing systems can expect the containers 2 at precise predetermined positions when these are transferred to a processing station, which significantly reduces the automation effort.

For facilitating the insertion of the packaging structure 30 into the transport and packaging container 10 and its removal therefrom, access openings 29 are formed on two longitudinal sides of the packaging structure 30, which are used by gripping arms or the like to grip the packaging structure 30. As viewed in longitudinal or transverse direction of the packaging structure 30, the access openings 29 may be offset to one another, which further simplifies an unambiguous positioning of the packaging structure 30 in the transport and packaging container 10.

The upper end of the transport and packaging container 10, and if necessary also the lower end of the transport and packaging container 10 may be sealed sterile against the environment by a protective foil, in particular by a meshwork of synthetic fibers such as polypropylene fibers (PP) or by a Tyvek® protective foil, as described above in connection with the packaging structure.

As will be readily apparent for the person skilled in the art upon reading the above description, a further aspect of the present invention relates to the use of a protective foil as described above and exemplified in FIGS. 6*a* and 6*b* for sterile packaging a plurality of containers for medical, pharmaceutical or cosmetic applications in a packaging structure or in a method as described above.

It will be readily apparent for the person skilled in the art upon reading the above description that the various aspects and features of the embodiments described above may be combined in any manner with one another, resulting in numerous further embodiments and modifications. It will be readily apparent for the person skilled in the art upon reading the above description that all such further embodiments and modifications shall be comprised by the present invention, as long as these do not depart from the general solution and scope of the present invention, as defined in the appended claims.

The invention claimed is:

1. A packaging structure for sterile packaging of a plurality of containers for medical, pharmaceutical or cosmetic applications, which are accommodated in the packaging structure and sterile packaged against the environment, comprising:
    a carrier in which a plurality of receptacles are formed;
    a plurality of containers which are each accommodated individually in the receptacles; and
    a gas-impermeable protective foil, which is connected to an upper surface of the carrier for sealing the receptacles sterile against the environment, wherein
    the receptacles are each formed by a closed bottom and a circumferential side wall,
    upper ends of the receptacles opposite to respective bottoms are open,
    circumferential connecting webs are provided at the upper ends of the receptacles, adjacent receptacles being connected to one another via the connecting webs,
    a protective foil is connected to the connecting webs along the connecting webs,
    at least one gas-permeable portion associated with the receptacles is formed in the protective foil and as a portion of the protective foil, so that the receptacles of the packaging structure can be sterilized by a gas flowing through the at least one gas-permeable portion,
    the connecting webs are configured and connected with the protective foil in such a manner that individual packaging subunits can be severed by severing along the connecting webs, each packaging subunit having one receptacle in which a single container is accommodated and sealed sterile against the environment by the protective foil, and
    all the receptacles of the packaging structure are each packaged individually, sterile and sealed against the at least one gas-permeable portion by bonding the protective foil along the connecting webs so that an interior of the receptacles does not communicate with the at least one gas-permeable portion.

2. The packaging structure according to claim 1, wherein each receptacle is associated with one gas-permeable portion.

3. The packaging according to claim 2, further comprising a recess that extends from the interior of the respective receptacle to the associated gas-permeable portion in the upper surface of the carrier and/or in a lower surface of the protective foil, which is plugged along the connecting webs after bonding the protective foil so that the receptacles are each sterile packaged and sealed against respective associated gas permeable portion.

4. The packaging structure according to claim 1, wherein
    the at least one gas-permeable portion of the protective foil is formed of a meshwork made of synthetic fibers or of a portion having a grid-like structure with openings and
    wherein the at least one gas-impermeable portion of the protective foil is formed of a plastic or metal foil or a composite material from these materials.

5. The packaging structure according to claim 4, wherein the meshwork made of synthetic fibers is a meshwork of polypropylene fibers.

6. The packaging structure according to claim 1, wherein the packaging structure is formed of a material which is resistant to hydrogen peroxide vapor.

7. The packaging structure according to claim 1, further comprising weakening regions that extend along the connecting webs along which the connecting webs can be separated mechanically so that the individual packaging subunits can be severed by severing along the weakening regions of the connecting webs.

8. The packaging structure according to claim 7, wherein the weakening regions extend in a middle along the connecting webs.

9. The packaging structure according to claim 7, wherein the weakening regions are formed as continuous, linear recesses or as a series of point-like recesses.

10. The packaging structure according to claim 9, wherein the weakening regions are formed by one of mechanical carving, embossing, and laser treatment of the material of the connecting webs.

11. The packaging structure according to claim 1, wherein
    the at least one gas-permeable portion of the protective foil is formed of a meshwork made of synthetic fibers or of a portion having a grid-like structure with openings and
    wherein the at least one gas-impermeable portion of the protective foil is formed of a plastic or metal foil or a composite material from these materials.

12. The packaging structure according to claim 11, wherein the meshwork made of synthetic fibers is a meshwork of polypropylene fibers.

13. The packaging structure according to claim 1, wherein the packaging structure is formed of a material which is resistant to hydrogen peroxide vapor.

14. The packaging structure according to claim 7, wherein
    the at least one gas-permeable portion of the protective foil is formed of a meshwork made of synthetic fibers or of a portion having a grid-like structure with openings and
    wherein the at least one gas-impermeable portion of the protective foil is formed of a plastic or metal foil or a composite material from these materials.

15. The packaging structure according to claim 14, wherein the meshwork made of synthetic fibers is a meshwork of polypropylene fibers.

* * * * *